United States Patent [19]

Caufield et al.

[11] Patent Number: 5,023,262
[45] Date of Patent: Jun. 11, 1991

[54] HYDROGENATED RAPAMYCIN DERIVATIVES

[75] Inventors: Craig E. Caufield, Plainsboro, N.J.; John H. Musser, Yardley; James M. Rinker, Reading, Pa.

[73] Assignee: American Home Products Corporation, New York, N.Y.

[21] Appl. No.: 567,858

[22] Filed: Aug. 14, 1990

[51] Int. Cl.$^5$ .................. A61K 31/395; C07D 491/16
[52] U.S. Cl. .................... 514/291; 540/456; 546/90
[58] Field of Search .......................... 540/456; 546/90; 514/291

[56] References Cited

U.S. PATENT DOCUMENTS

| | | | |
|---|---|---|---|
| 3,929,992 | 12/1975 | Sehgal | 424/122 |
| 3,993,749 | 11/1976 | Sehgal | 424/122 |
| 4,316,885 | 2/1982 | Rakhit | 424/122 |
| 4,401,653 | 4/1983 | Eng | 424/114 |
| 4,650,803 | 3/1987 | Stella | 514/291 |
| 4,885,171 | 12/1989 | Surendra | 424/122 |

OTHER PUBLICATIONS

J. Antibiot. 28, 721–726 (1975).
J. Antibiot. 28, 727–732 (1975).
J. Antibiot. 31, 539–545 (1978).
Can. J. Physiol. Pharmacol. 55, 48 (1977).
FASEB 3, 3411 (1989).
FASEB 3, 5256 (1989).
Lancet, 1183, (1978).
Can. J. Chem. 58, 579 (1980).

Primary Examiner—Robert T. Bond
Attorney, Agent, or Firm—Richard K. Jackson

[57] ABSTRACT

A derivative of rapamycin where one, two, or three of the double bonds at the 1-,3-, or 5-positions of rapamycin have been reduced to the corresponding alkane, or a pharmaceutically acceptable salt thereof, which by virtue of its antifungal activity is useful in treating fungal infections.

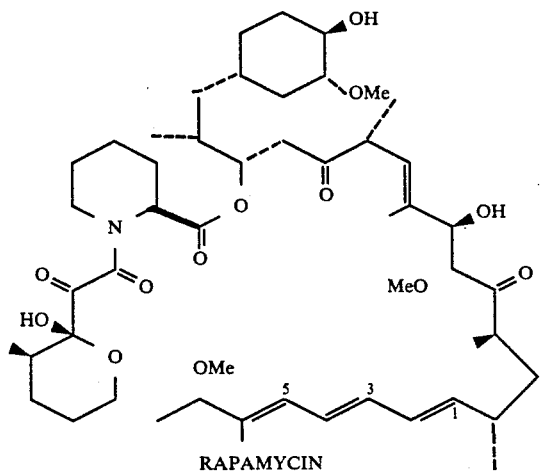

6 Claims, No Drawings

HYDROGENATED RAPAMYCIN DERIVATIVES

BACKGROUND

1. Field of the Invention

This invention relates to hydrogenated derivatives of rapamycin and a method for using them in the treatment of fungal infections.

2. Prior Art

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. Nos. 3,929,992; and 3,993,749]. The preparation of 1,3,5,29-octahydrorapamycin (perhydrorapamycin) was disclosed by J. A. Finlay et al., Can J. Chem. 58, 579 (1980).

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989), rapamycin has been shown to be effective in inhibiting transplant rejection (U.S. patent application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to C.A. nomenclature, the esters described above would be at the 31- and 42-positions.

DESCRIPTION OF THE INVENTION

This invention provides hydrogenated derivatives of rapamycin which are useful as antifungal agents possessing the general structure of rapamycin where one, two, or three of the double bonds at the 1-, 3-, or 5-positions of rapamycin have been reduced to the corresponding alkane, or a pharmaceutically acceptable salt thereof.

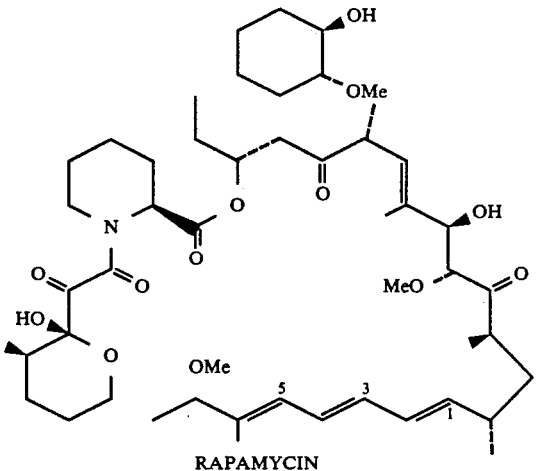

RAPAMYCIN

The pharmaceutically acceptable salts may be formed from inorganic cations such as sodium, potassium, and the like.

The compounds of this invention can be prepared from rapamycin by conventional methods disclosed in the literature using reagents that are either described in the literature or are commercially available. Hydrogenation over a palladium or platinum catalyst can be used to produce derivatives of rapamycin fully saturated at the 1, 3, and 5-positions, whereas the partially hydrogenated derivatives can be synthesized selectively using a rhodium catalyst, such as tris-(triphenylphosphine) rhodium (I) chloride during the hydrogenation.

Antifungal activity of the compounds of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC (μg/ml) to inhibit growth.

TABLE 1*

| Compound | Strain of *Candida albicans* | | | | |
|---|---|---|---|---|---|
| | ATCC 10231 | ATCC 38246 | ATCC 38247 | ATCC 38248 | 3669 |
| Example 1 | 0.4 | 0.2 | >0.4 | 0.2 | 0.2 |
| Example 2 | 0.006 | 0.05 | 0.006 | 0.0125 | 0.0125 |
| Rapamycin | 0.003 | 0.025 | 0.003 | 0.006 | 0.025 |

*expressed as MIC (μg/ml)

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio:

$$\frac{{}^3\text{H-control thymus cells} - \text{H}^3\text{-rapamycin-treated thymus cells}}{{}^3\text{H-control thymus cells} - \text{H}^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{{}^3\text{H-PLN cells control C3H mouse} - {}^3\text{H-PLN cells rapamycin-treated C3H mouse}}{{}^3\text{H-PLN cells control C3H mouse} - {}^3\text{H-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these 3 standard test procedures.

TABLE 2

| Compound | LAF Assay* (ratio) | PLN Assay* (ratio) | Skin Graft Assay (days + SD) |
|---|---|---|---|
| Example 1 | 0.31 | −1.67 | 7.3 ± 0.9 |
| Example 2 | 0.036 | + | 7.0 ± 0.9 |
| Rapamycin | 1.0 | 1.0 | 12.0 ± 1.7 |

*Calculation of ratios was described supra.
+Not evaluated

Surprisingly, compounds of the invention lacked the immunosuppressive activity associated with rapamycin, while still retaining a similar antifungal profile. The compounds of this invention were relatively inactive in both the in vitro LAF and in vivo PLN test procedures. When recipient mice were treated with compounds of this invention, the survival time of a transplanted pinch skin graft was comparable to the survival time observed in control mice (6–7 days).

The results of these standard pharmacological test procedures, show that the compounds of this invention have selective antifungal activity compared to rapamycin and are thus useful in the treatment of fungal infections.

The compounds may be administered neat or with a pharmaceutical carrier to a patient in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds may be employed as solutions, creams, or lotions by formulation with pharmaceutically acceptable vehicles containing 0.1-5 percent, preferably 2 percent of the agent which may be administered to the fungally affected area.

The following examples illustrate the preparation of representative compounds of this invention.

EXAMPLE 1

1,2-Dihydrorapamycin

A solution of 1 g (1.1 mmol) of rapamycin and 325 mg (351 μmol) of tris(triphenylphosphine) rhodium (I) chloride in 82 mL of benzene was hydrogenated at 50 psi for 4 days. The reaction was concentrated in vacuo affording a red foam. HPLC chromatography on a 2 inch column with 80% ethyl acetate/hexane as the eluant afforded 100 mg (10%) of 1,2-dihydrorapamycin as a white foam.

$^1$H NMR (CDCl$_3$, 400 MHz) δ6.292 (m, 1H, —C=CH—), 5.752 (m, 1H, —CH=CH—), 5.498 (m, 1H, —CH=CH—), 5.201 (m, 1H, —CH=CH—), 4.759 (s, 1H, —OH), 3.371 (s, 3H, CH$_3$O—), 3.368 (s, 3H, CH$_3$O—), 3.364 (s, 3H, CH$_3$O—); IR (KBr) 3430 (OH), 2940 (CH), 2885 (CH), 1740 (C=O), 1720 (C=O), 1650, 1455, 1380, 1200, 1160, 1100, 1000 cm$^{-1}$; MS (pos. ion FAB) 938 (m+Na), 429, 323, 217, 91 (100).

Analysis Calcd for C$_{51}$H$_{81}$NO$_{13}$: C 66.86; H 8.91; N 1.53. Found: C 66.72; H 9.05; N 1.19.

EXAMPLE 2

1,2,3,4-Tetrahydrorapamycin

A solution of 1 g (1.1 mmol) of rapamycin and 325 mg (351 μmol) of tris(triphenylphosphine) rhodium (I) chloride in 82 mL of benzene was hydrogenated at 50 psi for 4 days. The reaction was concentrated in vacuo affording a red foam. HPLC chromatography on a 2 inch HPLC column with 80% ethyl acetate/hexane as the eluant afforded 100 mg (10%) of 1,2,3,4-tetrahydrorapamycin as a white foam.

$^1$H NMR (CDCl$_3$, 400 MHz) δ5.435 (m, 3H, —C=CH—), 4.941 (s, 1H, —OH), 3.371 (s, 3H, CH$_3$O—), 3.368 (s, 3H, CH$_3$O—), 3.364 (s, 3H, CH$_3$O—); IR (KBr) 3430 (OH), 2940 (CH), 2885 (CH), 1745 (C=O), 1720 (C=O), 1650, 1455, 1380, 1200, 1160, 1100, 1000 cm$^{-1}$; MS (neg. ion FAB) 917 (M−), 594, 327, 167 (100), 128.

Analysis Calcd for C$_{51}$H$_{85}$NO$_{13}$.2H$_2$O: C 64.15; H 9.19; N 1.47. Found: C 64.15; H 8.88; N 1.32.

What is claimed is:

1. A derivative of rapamycin where one, two, or three of the double bonds at the 1-, 3-, or 5-positions of rapamycin have been reduced to the corresponding alkane or a pharmaceutically acceptable salt thereof.

2. A compound of claim 1 which is 1,2-dihydrorapamycin or a pharmaceutically acceptable salt thereof.

3. A compound of claim 1 which is 1,2,3,4-tetrahydrorapamycin or a pharmaceutically acceptable salt thereof.

4. A method of treating fungal infections by administering an effective amount of a compound which is a derivative of rapamycin in which one, two, or three of the double bonds at the 1-, 3-, or 5-positions have been reduced to the corresponding alkane or a pharmaceutically acceptable salt thereof.

5. A pharmaceutical composition comprising a compound of claim 1 or a pharmaceutically acceptable salt thereof and a pharmaceutically acceptable carrier.

6. A composition as claimed in claim 5, in unit dosage form.

* * * * *

UNITED STATES PATENT AND TRADEMARK OFFICE
CERTIFICATE OF CORRECTION

PATENT NO. : 5,023,262

DATED : June 11, 1991

INVENTOR(S) : Craig E. Caufield, John H. Musser, James R. Rinker

It is certified that error appears in the above-identified patent and that said Letters Patent is hereby corrected as shown below:

Title page, col. 2 and

Column 2, correct structure to show the following :

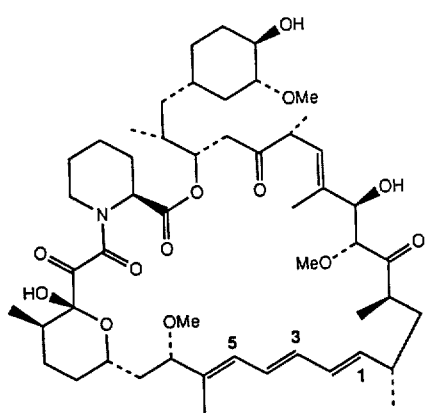

RAPAMYCIN

Signed and Sealed this

Twentieth Day of October, 1992

Attest:

DOUGLAS B. COMER

Attesting Officer

Acting Commissioner of Patents and Trademarks